United States Patent
Lee et al.

(10) Patent No.: US 9,597,366 B2
(45) Date of Patent: Mar. 21, 2017

(54) ANTICANCER COMPOSITION CONTAINING HERBAL EXTRACT

(75) Inventors: Jai-Heon Lee, Busan (KR); Kyoung-Sook Kim, Busan (KR); Young-Choon Lee, Busan (KR); Chang-Woo Cho, Gyeongsangnam-do (KR); KyoungMee Kim, Busan (KR); Young Soo Chung, Busan (KR)

(73) Assignee: DONG-A UNIVERSITY RESEARCH FOUNDATION FOR INDUSTRY-ACADEMY COOPERATION, Busan (KR)

( * ) Notice: Subject to any disclaimer, the term of this patent is extended or adjusted under 35 U.S.C. 154(b) by 1915 days.

(21) Appl. No.: 12/789,542

(22) Filed: May 28, 2010

(65) Prior Publication Data

US 2011/0293754 A1    Dec. 1, 2011

(51) Int. Cl.

| A61K 36/734 | (2006.01) |
|---|---|
| A61K 36/232 | (2006.01) |
| A61K 36/254 | (2006.01) |
| A61K 36/286 | (2006.01) |
| A61K 36/287 | (2006.01) |
| A61K 36/46 | (2006.01) |
| A61K 36/482 | (2006.01) |
| A61K 36/484 | (2006.01) |
| A61K 36/488 | (2006.01) |
| A61K 36/537 | (2006.01) |
| A61K 36/54 | (2006.01) |
| A61K 36/65 | (2006.01) |

(52) U.S. Cl.
CPC .......... *A61K 36/734* (2013.01); *A61K 36/232* (2013.01); *A61K 36/254* (2013.01); *A61K 36/286* (2013.01); *A61K 36/287* (2013.01); *A61K 36/46* (2013.01); *A61K 36/482* (2013.01); *A61K 36/484* (2013.01); *A61K 36/488* (2013.01); *A61K 36/537* (2013.01); *A61K 36/54* (2013.01); *A61K 36/65* (2013.01)

(58) Field of Classification Search
None
See application file for complete search history.

(56) References Cited

FOREIGN PATENT DOCUMENTS

KR    2009094637 A    * 9/2009

OTHER PUBLICATIONS

Hampton, Clinical Trials Probe New Therapies for some difficult-to-treat cancers, 2008, JAMA, 300: 384-385.*
Freedman, Congenital Marrow Failure Syndromes and Malignant Hematopoietic Transformation, 1996, The Oncologist, 1: 354-360.*
Demeule, M et al. Matrix metalloproteinase inhibition by green tea catechins. Biochimica et Biophysica Acta, vol. 1478, pp. 51-60, 2000.
Chung, TW et al. Novel and therapeutic effect of caffeic acid and caffeic acid phenyl ester on hepatocarcinoma cells: complete regression of hepatoma growth and metastasis by dual mechanism. The FASEB Journal, vol. 18, pp. 1670-1681, Nov. 2004.
Cho, HJ et al. Ascofuranone suppresses PMA-mediated matrix metalloproteinase-9 gene activation through the Ras/Raf/MEK/ERK- and Ap1-dependent mechanisms. Carcinogenesis, vol. 28, No. 5, pp. 1104-1110, 2007.
Moon, SK et al. ERK1/2 Mediates TNF-a-Induced Matrix Metalloproteinase-9 Expression in Human Vascular Smooth Muscle Cells Via the Regulation of NF-kB and AP-1: Involvement of the Ras Dependent Pathway. Journal of Cellular Physiology, vol. 198, pp. 417-427, 2004.
Woo, JH et al. Dykellic Acid Inhibits Phorbol Myristate Acetate-induced Matrix Metalloproteinase-9 Expression by Inhibiting Nuclear Factor κB Transcriptional Activity. Cancer Research, vol. 63, pp. 3430-3434, Jun. 15, 2003.

* cited by examiner

*Primary Examiner* — Terry A McKelvey
*Assistant Examiner* — Catheryne Chen
(74) *Attorney, Agent, or Firm* — Tristan A. Fuierer; Moore & Van Allen, PLLC

(57) ABSTRACT

The present invention relates to the anticancer composition containing an effective amount of herbal extract, and more particularly to the anticancer composition containing an effective amount of extract of *Salviae Miltiorrhizae Radix*, *Chrysanthemum indicum*, *Acanthopanax senticosus*, *Cinnamomum cassia Blume*, *Eucommia ulmoides Oliv.*, *Glycyrrhiza uralensis Fisch*, *Pueraria thunbergiana Benth*, *Crataegus pinnatifida Bunge*, *Cassia tora*, *Carthamus tinctorius L.*, *Paeonia lactiflora Pall*, and *Angelica gigas Nakai*. The anticancer composition containing an effective amount of herbal extract has advantage of minimal or few side effects and cytotoxicity as compared to many existing anticancer drugs having cytotoxicity and side effects.

6 Claims, 7 Drawing Sheets

ANTICANCER COMPOSITION CONTAINING HERBAL EXTRACT

BACKGROUND OF THE INVENTION (a) Field of the Invention

The present invention relates to the anticancer composition containing an effective amount of herbal extract, and more particularly to the anticancer composition is containing an effective amount of extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius L., Paeonia lactiflora Pall.* and *Angelica gigas Nakai.*

(b) Background of the Related Art

Metastasis is a complex series of steps including cancer cell growth, degradation of outer membrane protein, movement of cells into the circulatory system through basement membrane and the growth of secondary tumors at sites distant from a primary tumor.

The matrix metalloproteinases (MMPs) are a large family of zinc-dependent endoproteinases whose primary function is the degradation of proteins in the extracellular matrix (ECM). MMPs play a role in a wide range of tumoenesis, including early carcinogenic events, tumor growth, tumor invasion and metastasis.

Among the MMPs, the two gelatinase enzymes, MMP-2 (gelatinase A/72 kDa type IV collagenase) and MMP-9 (gelatinase B/92 kDa type IV collagenase) are key enzymes that participate in the degradation of type IV collagen, a major component of basement membrane (BM), and are considered to play critical functions in tumor progression during tumor invasion and metastasis. Although these two enzymes have similar substrate specificities, MMP-2 is constitutively expressed regardless of stimulation by cytokines or growth factors, whereas the synthesis and secretion of MMP-9 showing low expression levels in most cancer cells can be induced by a variety of stimuli, including cytokines, growth factors and phorbol 12-myristate 13-acetate (PMA) during various pathological processes such as tumor invasion, atherosclerosis, inflammation and arthritis.

The enhanced expression of MMP-2 and MMP-9 is correlated with increased metastatic potential in many cancer types including melanoma, breast, prostate and brain carcinomas, indicating that regulation of these enzyme activities is clearly a key step in tumor invasion.

Therefore, the inhibition of MMP-9, with the aim of suppressing tumor cell migration or invasion, could be a potential and effective therapeutic strategy for prevention and treatment of cancer metastasis.

A number of MMP inhibitors have been developed for the treatment of cancer and most of these MMP inhibitors including synthetic peptides, chemically modified tetracyclines, and bisphosphonates are reported to exert side effects such as musculoskeletal pain in tendons and joints.

Because a lot of anti-cancer medicines including MMP inhibitors have high cytotoxicity and side effects, recently, a traditional Chinese prescription is coming to the attention in new sauce of a anti-cancer medicine. Besides, possibility of medicinal herbs as treatment medicine is raised while molecular mechanisms suppressing expression and secretion of MMP-9 are known.

Accordingly, the present inventors have many efforts to develop composition which has excellent MMP inhibitory effects from herbal extracts, as result, have found that JNP-9, which is composed of 12 herbal ingredients specifically suppresses PMA-induced MMP-9 expression, thereby completing the present invention.

SUMMARY OF THE INVENTION

It is, therefore, an object of the invention to provide the anticancer composition containing herbal ingredients which acts as MMP inhibitor.

To achieve the above-mentioned purpose, The present invention provides the anticancer composition containing an effective amount of extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius L., Paeonia lactiflora Pall.,* and *Angelica gigas Nakai.*

Another object of the present invention is to provide methods of preventing and/or treating a cancer in a subject comprising the step of administering the composition containing herbal ingredients which acts as MMP inhibitor to the subject.

Another object of the present invention is to provide methods of inhibiting MMP expression in a subject comprising the step of administering the composition containing herbal ingredients which acts as MMP inhibitor to the subject.

Other features and advantages of the present invention will be apparent from the additional descriptions provided herein including the different examples and claims.

DETAILED DESCRIPTION OF THE PREFERRED EMBODIMENT

Figure 1:
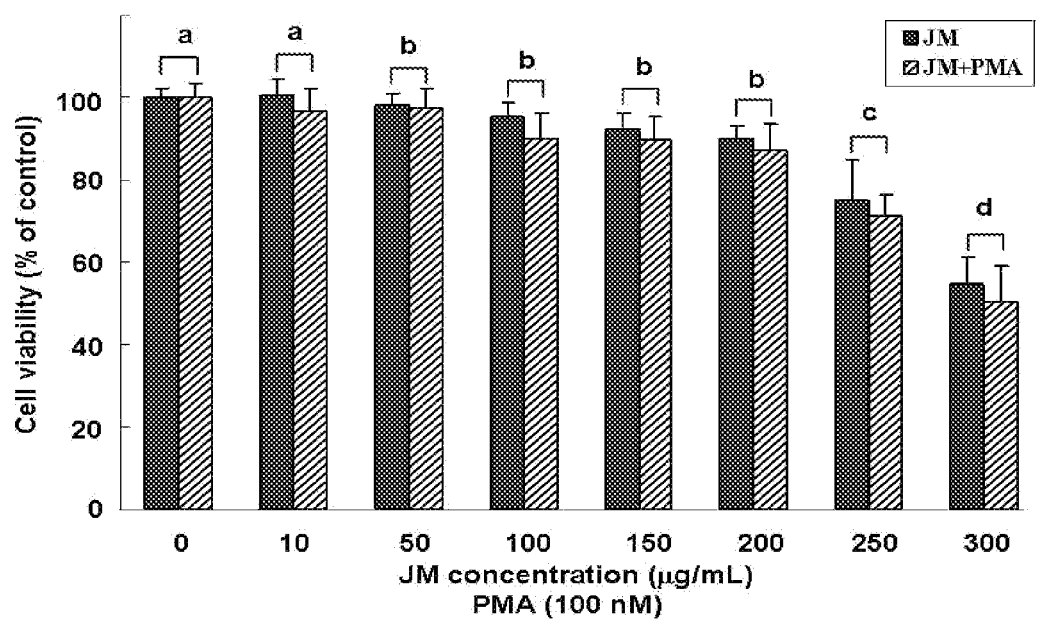
FIG. 1 shows cytotoxic effect of JM on viability of MCF-7 cells.

The present invention relates to the anticancer composition containing an effective amount of extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius L., Paeonia lactiflora Pall.* and *Angelica gigas Nakai.*

In the present invention, the extract is water or C1~C4 alcohol extract.

In one aspect, the present invention relates to the composition, (named as "JNP-9"), which is containing *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria*

*thunbergiana Benth, Crataegus pinnatifida Bunge, Cassia tora, Carthamus tinctorius* L., *Paeonia lactiflora Pall.* and *Angelica gigas Nakai*, indicated in Table 1.

In the inventive composition, the composition contains the extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai* in an amount of 10-99% by weight, and preferably, 20-50% by weight, based on the total weight of the composition.

In the inventive composition, the composition contains the extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai*, at a weight ratio of 1:0.1-10:0.1-10:0.1-10:0.1-10:0.1-10:0.1-10:0.1-10:0.1-10: 0.1-10:0.1-10:0.1-10, respectively, but is not limited thereto.

The anticancer composition containing the extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai* may be formulated for oral administration (for example, oral dietary supplement) in the form of powders, granules, tablets, capsules, suspensions, emulsions, syrups or aerosols according to a conventional method. It may be formulated in the form of external preparations, suppositories or sterile injectable solutions. Carriers, excipients or diluents that can be included in the composition containing the extract include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrolidone, water, methyl hydroxybenzoate, propyl hydroxybenzoate, talc, magnesium stearate and mineral oils. For formulations, commonly used diluents or excipients such as fillers, expanders, bonding agents, wetting agents, disintegrants and surfactants, etc., are used. Solid formulations for oral administration include tablets, pills, powders, granules, capsules, etc. Such solid dosages are prepared by admixing the extract of the present invention with at least one excipient, such as starch, calcium carbonate, sucrose or lactose, gelatin, etc. In addition to simple expedients, lubricants such as magnesium styrate, talc, etc. may be added. Liquid formulations for oral administration, such as suspensions, internal solutions, emulsions, syrups, etc., may comprise simple diluents, e.g., water and liquid paraffin, as well as various excipients, e.g., humectants, sweeteners, aromatics, preservatives, etc. Formulations for parenteral administration include sterilized aqueous solutions, non-aqueous solvents, suspensions, emulsions, lyophilized agents, suppositories, etc. Non-aqueous solvents and suspensions may be prepared using vegetable oils, such as propylene glycol and polyethylene glycol, olive oil, or using injectable esters such as ethyloleate. As a base for suppositories, Witepsol, Macrogol, Tween 61, cacao fat, laurin fat, glycerogelatin, etc. may be used.

In one embodiment of the present invention, "JM" is the methanolic extract of "JNP-9". JNP-9 powder were extracted 3 times with methanol at 60° C. for 5 h. The methanolic extract was filtered through a Whatman No. 1 filter paper (Advantec, Tokyo, Japan) and then concentrated under reduced pressure using a rotary evaporator, after which it was lyophilized. and the methanolic extract of JNP-9 (JM) was dissolved in dimethyl sulfoxide (DMSO).

In one embodiment of the present invention, JM didn't show cytotoxic effects on the proliferation of MCF-7 human breast carcinoma cells at a concentration 200 µg/ml and belows but showed weak cytotoxic effects at a concentration of 300 µg/ml.

In one embodiment of the present invention, MMP-9 activity in the conditioned medium of MCF-7 cells was dramatically induced by treatment with PMA. and JM inhibited PMA-induced MMP-9 activity in the PMA-induced MCF-7 cells after JM treatment in a dose-dependent manner. These results obtained on the zymography and Western blot analysis.

Furthermore, RT-PCR assay demonstrated that treatment of cells with JM dramatically decreased the levels of PMA-stimulated MMP-9 mRNA expression in a dose-dependent manner, and promoter assay demonstrated that JM specifically suppressed PMA-induced MMP-9 expression through inhibition of its transcriptional activity in MCF-7 cells.

In the one embodiment of present invention, to examine whether the treatment of cells with JM affected the invasion of PMA-induced MCF-7 cells, cell invasion assays were carried out in Transwells coated with Matrigel containing extracellular matrix proteins. The invasion of MCF-7 cells was significantly increased by treatment with PMA when compared to PMA-untreated control cells. However, JM treatment markedly inhibited the PMA-stimulated invasion of MCF-7 cells in a dose-dependent manner.

In one embodiment of the present invention, to investigate which of these transcriptional factors are involved in the inhibition of the MMP-9 transcription by JM, MCF-7 cells were transiently transfected with luciferase reporter plasmids linked to promoter with mutations in two AP-1 sites, or the NF-κB binding site and carried out promoter assay. As a result, JM dramatically decreased AP-1 binding activity induced by PMA, but it did not affect the PMA-induced binding activity of NF-κB. These data suggest that JM inhibits PMA-induced MMP-9 expression by decreasing DNA binding activity of AP-1.

In one embodiment of the present invention, to elucidate which of these signal transduction pathways are involved in PMA-stimulated MMP-9 expression and JM-mediated inhibition of the MMP-9 expression in MCF-7 cells, the effects of specific kinase inhibitors of these signaling pathways on the expression of MMP-9 in PMA-induced MCF-7 cells using gelatin zymography and western blot analysis were examined. As a result, The treatment of JM specifically decreased ERK1/2 phosphorylation in a does-dependent manner, whereas the phosphorylation levels of JNK and p38 MAPK were slightly decreased by JM. These data suggest that the specific inhibition of ERK1/2 signaling pathway are directly involved in the regulation of PMA-induced MMP-9 expression by JM.

In another aspect of the present invention, the anticancer composition according to the present invention can be used in a method for preventing and/or treating a cancer in a subject by administering the composition to the subject.

In detail, the composition of the present invention can be administered orally and be used in general forms of pharmaceutical formulation. The composition of the invention can additionally include, in addition to the extracts, one or more active ingredients having the same or similar functions. The composition of the present invention can also include, in addition to the above-mentioned active ingredients, one or more pharmaceutically acceptable carriers for the administration. The pharmaceutically acceptable carrier can be selected or be prepared by mixing more than one ingredients selected from the group consisting of saline, sterilized water, buffered saline, dextrose solution, malto-dextrose solution, glycerol and ethanol. Other general additives such as anti-oxidative agent, buffer solution, bacteriostatic agent, etc, can be added. Also, in order to prepare powders, tablets, capsules, granules or granules such as solutions, suspension and emulsions, diluents, dispersing agents, surfactants, binders and lubricants can be additionally added. The composition of the present invention can further be prepared in suitable forms for each disease.

The cancer herein can be selected from the group consisting of breast cancer, laryngeal cancer, lung cancer, esophageal cancer, pancreatic cancer, large intestine cancer, liver cancer, stomach cancer, tongue cancer, skin cancer, brain cancer, uterine cancer, cervical cancer, ovarian cancer, kidney cancer, gallbladder cancer, oral cancer, colon cancer and bladder cancer, but not always limited thereto.

In another aspect of the present invention, the anticancer composition according to the present invention can be used in a method for inhibiting MMP expression in a subject by administering the composition to the subject.

EXAMPLES

Hereinafter, the present invention will be described in further detail with reference to examples. It is to be understood, however, that these examples are for illustrative purposes only and are not to be construed to limit the scope of the present invention.

Example 1

Preparation of Methanolic Extract of JNP-9 (JM)

All herbs composing JNP-9 were purchased from an oriental drug store (Jungdo, Inc. Seoul, Korea). The medication is containing twelve herbal ingredients and the crude drug composition of JNP-9 is indicated in Table 1.

TABLE 1

Mixture of a traditional Korean formulation, JNP-9

| Medicinal herbal name | Scientific name | Part used | Dose amount (g) | Ratio (%) |
|---|---|---|---|---|
| Salvia miltiorrhiza | Salviae Miltiorrhizae Radix | Root | 2.3 | 11.0 |
| Chrysanthemum | Chrysanthemum indicum | Flower | 2.7 | 12.9 |
| Eleuthero | Acanthopanax senticosus | Seeds | 2.0 | 9.5 |
| Cinnamomi Ramulus | Cinnamomum cassia Blume | Bark | 1.3 | 6.2 |
| Eucommiae Cortex | Eucommia ulmoides Oliv. | Bark | 0.7 | 3.3 |
| Licorice | Glycyrrhiza uralensis Fisch | Bark | 2.0 | 9.5 |
| Puerariae Radix | Pueraria thunbergiana Benth | Root | 2.3 | 10.9 |
| crataegi fructus | Crataegus pinnatifida Bunge | Seeds | 2.3 | 10.9 |
| Cassiae Semen | Cassia tora | Seeds | 1.7 | 8.1 |
| Safflower | Carthamus tinctorius L. | Flower | 1.7 | 8.1 |
| Peony Root | Paeonia lactiflora Pall. | Root | 1.0 | 4.8 |
| Dong quai | Angelica gigas Nakai | Root | 11.0 | 4.8 |
| Total | | | 21.0 | 100 |

Twenty grams of JNP-9 powder were extracted 3 times with methanol at 60° C. for 5 h. The methanolic extract was filtered through a Whatman No. 1 filter paper (Advantec, Tokyo, Japan) and then concentrated under reduced pressure using a rotary evaporator, after which it was lyophilized. The w/w yield of the methanol extract was 1.5 g. For the bioassays, the methanolic extract of JNP-9 (JM) was dissolved in dimethyl sulfoxide (DMSO) at a concentration of 100 ng/ml.

Example 2

The Cytotoxicity Assay of JM

MCF-7 cells were obtained from the American Type Culture Collection (ATCC; Manassas, Va., USA) and cultured in Dulbecco's modified Eagle medium (DMEM, Gibco-BRL, Rockville, Md., USA) supplemented with 10% fetal bovine serum (FBS), penicillin (100 U/ml) and streptomycin (100 μg/ml). The cell culture was maintained at 37° C. in a humidified atmosphere containing 5% $CO_2$. Cells were grown to sub-confluence and rinsed with phosphate-buffered saline (PBS) and then incubated in serum-free medium for 24 h. JM dissolved in DMSO was added to the culture medium so that the final concentration of DMSO was 0.1%.

The cytotoxic effect of the methanolic extract of JNP-9 (JM) on the viability of MCF-7 cells was investigated using a commercially available proliferation kit (XTT; Boehringer Mannheim, Mannheim, Germany).

Briefly, the cells were plated in 96-well culture plates at a density of $1 \times 10^4$ cells per well, in DMEM culture medium and incubated for 24 h. Then, the medium was removed and replaced with fresh DMEM culture medium containing various concentrations (0-300 μg/ml) of JM. After incubation for an additional 24 h, 50 μl of XTT reaction solution (sodium 3'-[1-(phenyl-aminocarbonyl)-3,4-tetrazolium]-bis (4-methoxy-6-nitro)benzenesulfonic acid hydrate and N-methyl dibenzopyrazine methyl sulfate; mixed in proportion 50:1) prepared by mixing 5 ml of XTT-labeling reagent and 100 μl of electron coupling reagent, was then added to each well. After 4 h of incubation at 37° C., the absorbance was measured on an ELISA plate reader (Bio-Rad, CA, USA) at the test wavelength of 490 nm. All determinations were confirmed by at least three identical and independent experiments.

As a result, as shown in FIG. 1, JM showed weak cytotoxic effects on the proliferation of MCF-7 cells in typical concentrations (IC50>300 μg/ml). Thus, JM was used up to 200 μg/ml in this study in order to exclude any cytotoxic effects it may otherwise have exerted.

Example 3

Inhibitory Effects of JM on MMP-9 Expression and Activity

To examine the inhibitory effects of JM on PMA-induced MMP-9 enzyme activity, the cultured conditioned media collected from MCF-7 cells in the presence or absence of PMA and JM (0, 50, 100, 150, and 200 μg/ml), were subjected to a gelatin zymography assay.

Briefly, MCF-7 cells were seeded onto 6-well tissue culture plates at a density of $10^5$/well in DMEM with 10% FBS and were cultured to sub-confluence. Cells were then washed with PBS and starved in serum-free medium. To stimulate MMP-9 expression, PMA (Phorbol myristrate acetate, Sigma, Boston, Mass., USA) was added to a final concentration of 100 nM, and then treated with or without various concentrations (0, 50, 100, 150, and 200 μg/ml) of JM. After 24 h incubation, conditioned medium obtained from PMA-induced various cells was collected. Gelatin zymography was performed (Demeule, M. et al., *Biochim, Biophys, Acta*, 1478:51, 2000).

Culture supernatants were resuspended in a sample buffer containing 62.5 mM Tris-HCl (pH 6.8), 10% glycerol, 2% SDS, and 0.00625% (w/v) bromophenol blue and loaded without boiling in 10% acrylamide/bisacrylamide (29:1), resolving gel containing 0.1% (w/v) gelatin.

Electrophoresis was carried out at a constant voltage of 180 V for 80 min. After electrophoresis, the gels were washed in 2.5% Triton X-100 (2×30 min) at room temperature, and subsequently incubated at 37° C. for 20 h in the incubation buffer containing 10 mM $CaCl_2$, 150 mM NaCl, and 50 mM Tris-HCl (pH 7.5). The gels were then stained in 0.1% Coomassie blue R-250 in 30% methanol and 10% acetic acid, and destained in the same solution without the Coomassie blue dye, after which the gels were photographed on a light box. Proteolysis was detected as a white zone in a dark blue field, and the intensity of the bands obtained from the zymogram studies was estimated with a Scion Image Instrument (Scion Corp., MD).

Figure 2:
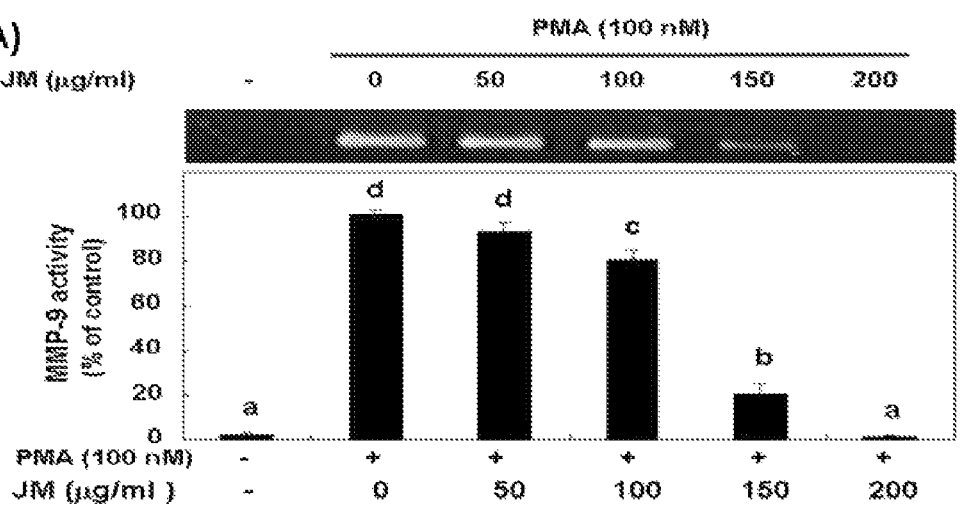
FIG. 2 shows effects of JM on the PMA-induced MMP-9 activity.
Figure 2:
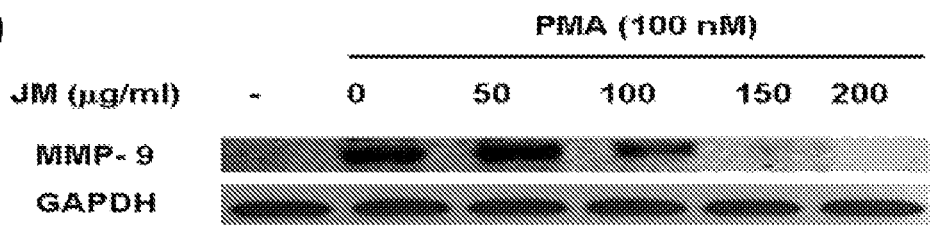

As shown in FIG. 2A, MMP-9 activity was undetectable in the medium from control cells untreated with PMA, whereas activity in the conditioned medium of MCF-7 cells was dramatically induced by treatment with PMA. JM significantly inhibited PMA-induced MMP-9 activity in a dose-dependent manner and the IC50 values calculated from semi-log was 130 µg/ml.

The result obtained on the zymography was further confirmed by Western blot analysis.

MCF-7 cells were treated with various concentrations (0, 50, 100, 150, and 200 µg/ml) of JM in the presence or absence of 100 nM PMA as indicated. The cells were then harvested for Western blot analysis to detect MMP-9 and GAPDH proteins.

Cellular lysates were prepared in a lysis buffer containing 50 mM Tris-HCl (pH 7.5), 150 mM NaCl, 2 mM ethylenediaminetetraacetic acid (EDTA), 1% Triton X-100, 0.1% sodium dodecyl sulfate (SDS), 10% glycerol, 0.5% deoxycholate, 1 mM NaF, 1 mM $Na_3VO_4$, 20 µg/ml phenyl methyl sulfonyl fluoride (PMSF), 1 µg/ml leupeptin, 1 µg/ml aprotinin. The cells were disrupted and extracted on ice for 10 min. After centrifugation at 13,000 rpm for 15 min, the supernatant was obtained as the cell lysate. Protein concentrations were measured using the Bradford assay. Aliquots of cellular proteins (20 µg per lane) were electrophoresed on 10% SDS-polyacrylamide gel electrophoresis (PAGE) and transferred to an Immobilon-P-membrane (Millipore, Bedford, Mass., USA). The membrane was blocked in 5% skim milk and then incubated with a MMP-9, specific antibody (Cell Signaling Technology, Danvers, Mass., USA), for 2 h. After washing, the membrane was incubated with an anti-rabbit secondary antibody conjugated with horseradish peroxidase. After the final washes, the membrane was developed using ECL chemiluminescence reagents (Amersham Arlington Heights, Ill., USA).

As a result, The amounts of MMP-9 protein in the cellular lysates of MCF-7 cells were gradually decreased in a dose-dependent manner, whereas GADPH expression was not affected by treatment with JM (FIG. 2B).

Example 4

Inhibitory Effects of JM on Transcription of MMP-9 Gene

To determine whether the inhibition of MMP-9 expression by JM was due to the decreased transcriptional level of MMP-9 gene, RT-PCR and promoter assays were performed using transiently transfected cells with a luciferase reporter gene linked to the MMP-9 promoter sequence.

(1) RT-PCR

To detect the expression of MMP-9, total RNA was isolated from MCF-7 cell of each kind, which was cultured in example 3, using the Trizol reagents (Invitrogen, Carlsbad, Calif., USA). For RT-PCR, cDNA was synthesized from 1 µg of total RNA using an AMV RNA PCR Kit (Takara, Japan). The cDNA was amplified by PCR with the following primers.

```
Sequence No. 1:
5'-GGA GCC GCT CTC CAA GAA GCT T-3'
(MMP-9 primer, 520 bp)

Sequence No. 2:
5'-CTC CTC CCT TTC CTC CAG AAC AGA A-3'
(MMP-9 primer, 520 bp)

Sequence No. 3:
5'-CAA GAG ATG GCC ACG GCT GCT-3'
(β-actin primer, 247 bp)

Sequence No. 4:
5'-TCC TTC TGC ATC CTG TCG GCA-3'
(β-actin primer, 247 bp)
```

Primers were used at a final concentration of 0.5 µM. The reaction mixture was first denatured at 94° C. for 1 min. PCR reactions were carried out by 30 cycles consisting of 94° C. for 30 s, 58° C. for 30 s and 72° C. for 42 s. PCR products were analyzed by 1.5% agarose gel electrophoresis. The intensity of the bands obtained from the RT-PCR product was estimated with a Scion Image Instrument (Scion Corp., MD).

Figure 3:
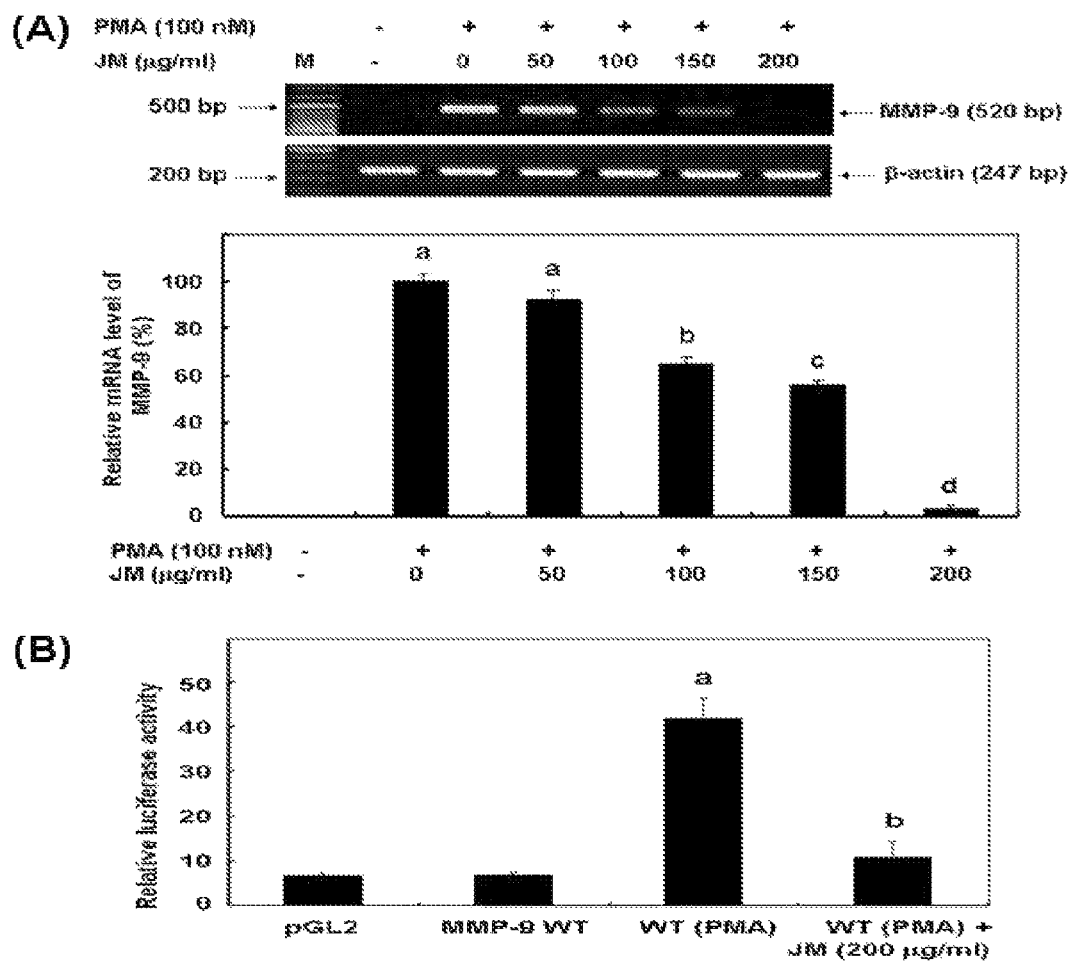
FIG. 3 shows effects of JM on the PMA-induced transcriptional activation of MMP-9 gene in MCF-7 cells.

As a result, Treatment of cells with JM dramatically decreased the levels of PMA-stimulated MMP-9mRNA expression in a dose-dependent manner (FIG. 3A). On the other hand, β-actin mRNA expression was not affected by the treatment of cells with JM (200 µg/ml).

(2) Promoter Assay

MMP-9 Wild-Type Construct (pGL2-MMP-WT)

Cells were plated onto 6-well plates at a density of $2\times10^5$ cells per well and grown overnight. Cells were cotransfected with 1 µg of pGL2-MMP-WT and 1 µg of the pCMV β-galactosidase reporter plasmid for 5 h using Lipofectamine reagent (Invitrogen, San Diego, Calif., USA). After transfection, the cells were starved in serum-free media for 6 h, PMA was added to fresh serum-free media at a final concentration of 100 nM in the presence or absence of JM (200 µg/ml) and then cells were incubated for 24 h.

First, the cultured cells were harvested and were lysated in 200 µl of M-PER Mammalian protein extraction reagent (Pierce, Rockford, Ill., USA). Luciferase activity was assayed by using the luciferase enzyme assay system (Promega, USA).

Luciferase activity was normalized with the β-galactosidase activity in the cell lysate and expressed as an average of three-independent experiments.

As shown in FIG. 3B, luciferase activity was increased up to about 6.3-fold in cells treated with PMA as compared to untreated cells. Treatment of cells with JM (200 µg/ml) significantly decreased PMA-stimulated luciferase activity. These results indicated that JM specifically suppressed PMA-induced MMP-9 expression through inhibition of its transcriptional activity in MCF-7 cells.

Example 5

Inhibitory Effects of JM on Invasion of MCF-7 Cells

To examine whether the treatment of cells with JM affected the invasion of PMA-induced MCF-7 cells, cell invasion assays were carried out in Transwells coated with Matrigel containing extracellular matrix proteins.

Matrigel-coated filter inserts (8 µm pore size, Becton-Dickinson, USA) were fit into 24-well Transwell chambers, and then MCF-7 cells were tested for their invasive ability through a basement membrane Matrigel in vitro in Transwell chambers (Corning Coster, Cambridge, Mass., USA).

MCF-7 cells were detached from the tissue culture plates, washed, resuspended in conditioned medium with various concentration (0, 100, and 200 µg/ml) of JM in the presence or absence of PMA, and then seeded into the upper compartment of the invasion chamber. Conditioned medium (500 µl) was added to the lower compartment of the invasion chamber. Matrigel invasion chambers were incubated for 24 h at 37° C. in 5% $CO_2$. After incubation, the filter inserts were removed from the wells, and non-invading cells on the upper surface of the filter were removed by wiping with a cotton swab. The filters were fixed, stained and according to the manufacturer's instructions (Becton-Dickinson). The cells that invaded the Matrigel were located on the filter surface. The filter was excised and then mounted on a microscopic slide for cell counting and photographic purposes.

Figure 4:
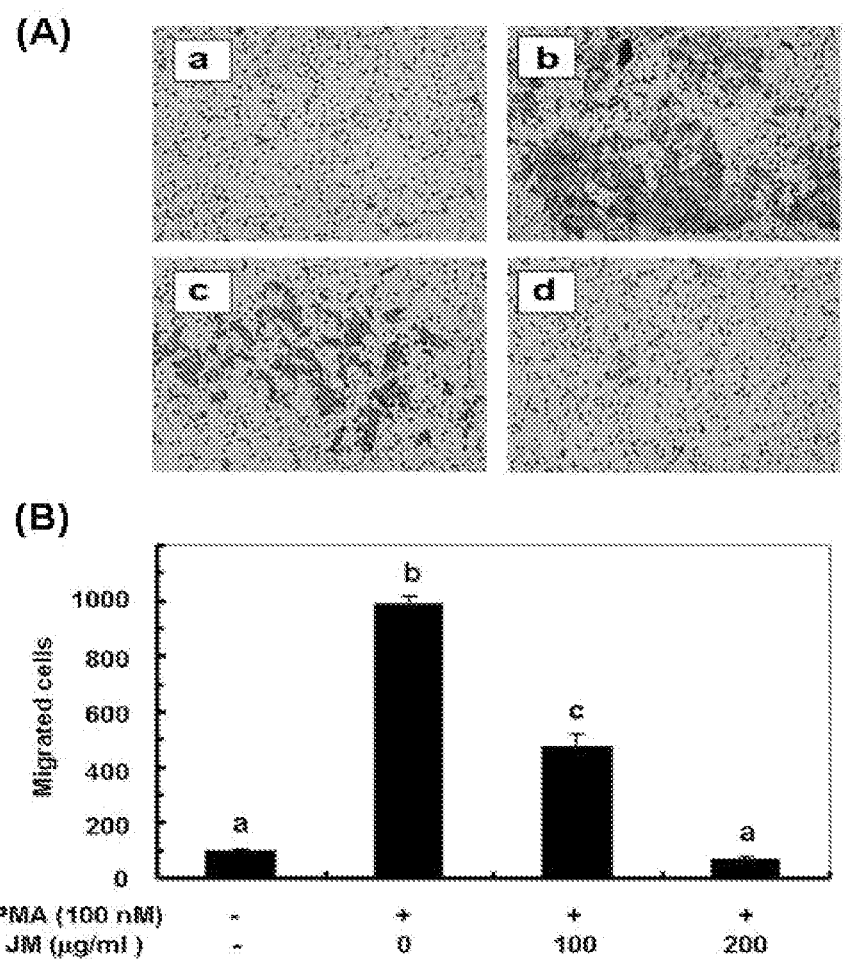
FIG. 4 shows effect of JM on PMA-induced invasion of MCF-7 cells.

As shown in FIG. 4, the invasion of MCF-7 cells was significantly increased by treatment with PMA when compared to PMA-untreated control cells. However, JM treatment markedly decreased the PMA-stimulated invasion of MCF-7 cells in a dose-dependent manner, reaching the basal level exhibited by the control cells at a concentration of 200 µg/ml.

These results suggested that JM could act as a potential anti-metastatic agent.

Example 6

Identification of JM-Responsive Element in PMA-Induced MMP-9 Promoter

It is generally known that human MMP-9 promoter contains cis-acting regulatory elements for transcription factors including two AP-1 sites (located at −79 bp and −533 bp) and an NF-kB site (located at −600 bp), which are pivotally involved in the induction of MMP-9 gene by PMA (Chung T W et al., *FASEB J.*, 18: 1670, 2004; Cho, H J et al., *Carcinogenesis*, 28:1104, 2007).

To investigate which of these transcriptional factors are involved in the inhibition of the MMP-9 transcription by JM, MCF-7 cells were transiently transfected with luciferase reporter plasmids linked to promoter with mutations in two AP-1 sites, or the NF-kB binding site.

AP-1 site-mutated MMP-9 (pGL2-MMP-9 mAP-1-2), and NF-kB site-mutated MMP-9 (pGL2-MMP-9 NF-kB) were used in transient transfection assays as described previously (Moon, S K et al., *J Cell Physiol*, 198:417, 2004; Chung, T W et al., *FASEB J.*, 18: 1670, 2004).

(1) Luciferase Reporter Assay

The AP-1 and NF-kB reporter constructs were purchased from Clontech (Palo Alto, Calif., USA).

Cells were plated onto 6-well plates at a density of $2\times10^5$ cells per well and grown overnight. Cells were cotransfected with 1 µg of various plasmid constructs (pGL2-MMP-9 mAP-1-2, pGL2-MMP-9 NF-kB) and 0.5 µg of the pCMV-β-galactosidase reporter plasmid for 5 h using Lipofectamine reagent (Invitrogen, San Diego, Calif., USA). After transfection, the cells were starved in serum-free media for 6 h. PMA was added to fresh serum-free media at a final concentration of 100 nM in the presence or absence of JM (200 µg/ml) and then cells were incubated for 24 h.

Cells were lysated in 200 µl of M-PER mammalian protein extraction reagent (Pierce, Rockford, Ill., USA). Luciferase activity was assayed by using the luciferase assay system (Promega, Madison, Wis., USA).

Luciferase activity was normalized with the β-galactosidase activity in the cell lysate, and was determined as an average of three-independent experiments.

Figure 5:
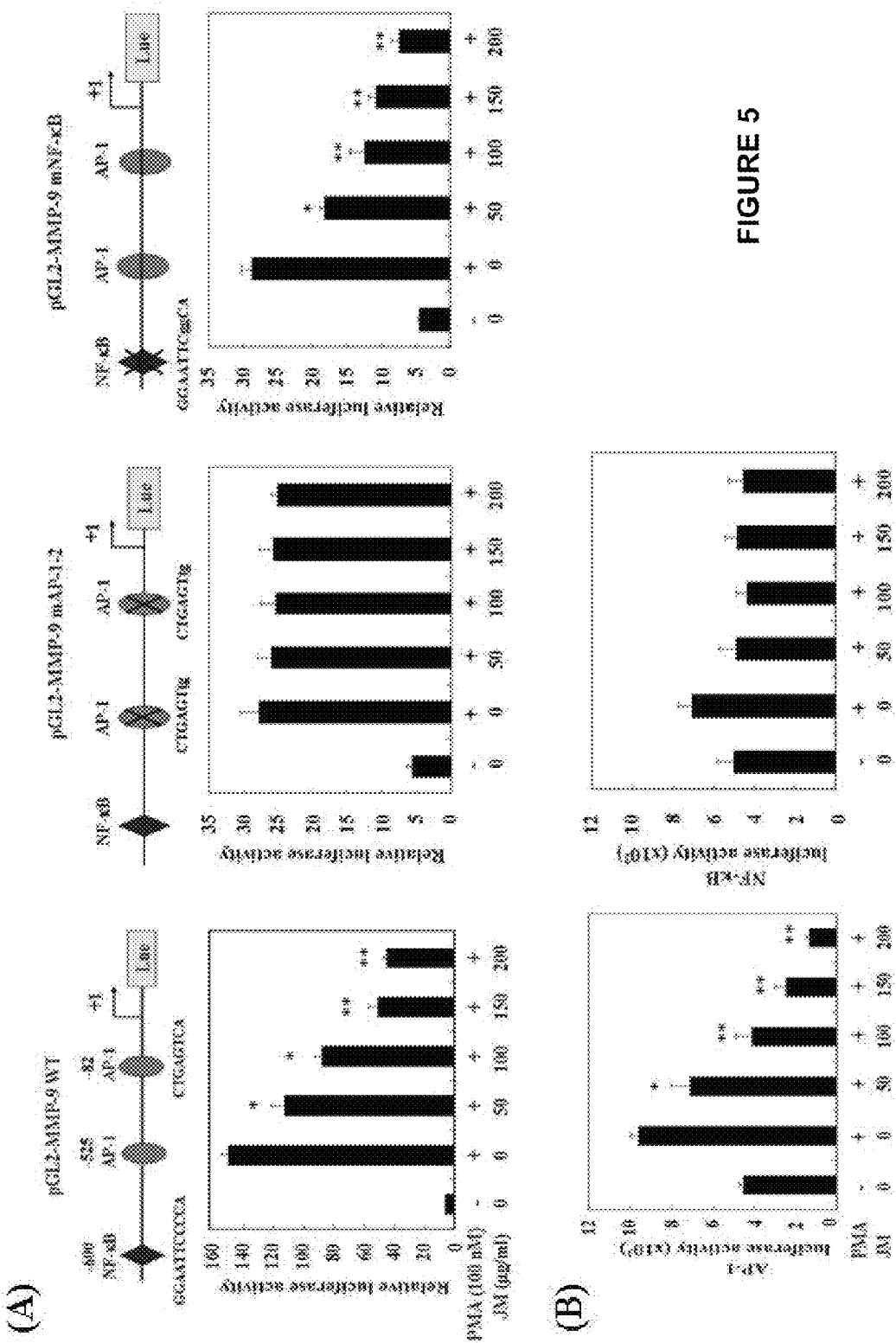
FIG. 5 shows effects of JM on the PMA-induced promoter activation of MMP-9 gene.

As shown in FIG. 5A, the mutation of the AP-1 binding sites markedly decreased the response to PMA, compared to the wild type. The mutation in the NF-kB binding site also reduced PMA-induced MMP-9 reporter gene activity. Treatment with JM in the presence of PMA resulted in the significant decrease in the transcription activity of the reporter with the NF-kB mutation, but was not effective for the transcription activity of the reporter with AP-1 mutations, suggesting that the major target of JM is the AP-1 transcription factors.

To confirm the specificity of JM-mediated inhibitory effect on AP-1, MCF-7 cells were transiently transfected with luciferase reporter plasmids including the tandem repeat of the AP-1, or NK-kB binding sites. Treatment with JM significantly decreased the luciferase activity in the cells transfected with the AP-1 reporter plasmid in a dose-dependent manner, whereas the luciferase activity of cells transfected with NF-kB reporter plasmid was not markedly affected by JM (FIG. 5B).

(2) EMSA (Electrophoretic Mobility Shift Assay)

To further verify whether JM inhibits PMA-induced MMP-9 expression by blocking the AP-1 activation in MCF-7 cells, EMSA was performed using double-stranded $^{32}$P-labeled oligonucleotide fragments containing the consensus sequences for AP-1 and NF-kB as probes and analyzed for DNA binding activities of AP-1 and NF-kB.

MCF-7 cells were incubated in the presence or absence of PMA with different concentrations of JM for 24 h, and nuclear extracts were prepared (Chung, T W et al., *FASEB J.*, 18: 1670, 2004) and the protein concentrations of the extracts were determined using Bio-Rad protein assay kit. To determine the activations of AP-1 and NF-kB, EMSA was performed using a gel shift assay system kit (Promega, Madison, Wis., USA).

Briefly, double-stranded oligonucleotides containing the consensus sequences for AP-1 and NF-kB were end-labeled with [g$^{32}$-P]ATP (3000 Ci/mmol; Amersham Pharmacia Bioteck) using T4 polynucleotide kinase and used as probes for EMSA.

```
Sequence No. 5:
5'-TGACCCCTGAGTCAGCACTT-3'
(AP-1 probe sequence)

Sequence No. 6:
5'-CCAGTGGAATTCCCCAG-3'
(NF-kB probe sequence)
```

Competition was performed using either 100-fold excess of an unlabeled AP-1 or NF-kB consensus oligonucleotides. Nuclear extract proteins (2 µg) were preincubated with the gel shift binding buffer [4% glycerol, 1 mM $MgCl_2$, 0.5 mM EDTA, 0.5 mM DTT, 50 mM NaCl, 10 mM Tris-HCl (pH 7.5), and 0.05 mg/ml poly dI/dC (deoxyinosine-deoxycytosine)] for 10 min, then incubated with the labeled probe for 20 min at room temperature. Each sample was electrophoresed in a 4% nondenaturing polyacrylamide gel in 0.5×TBE buffer at 300 Volt for 15 min. The gel was dried and exposed to X-ray film overnight.

Figure 6:
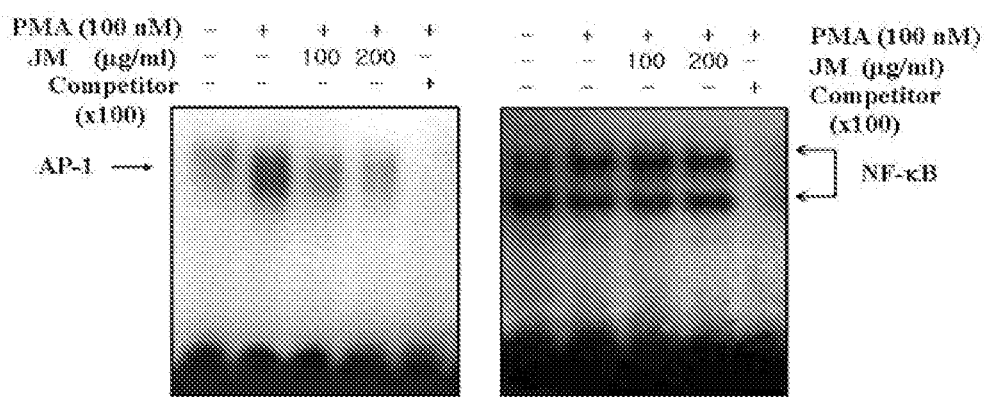
FIG. 6 shows effects JM on the PMA-induced AP-1 and NF-kB activity.
Figure 6:
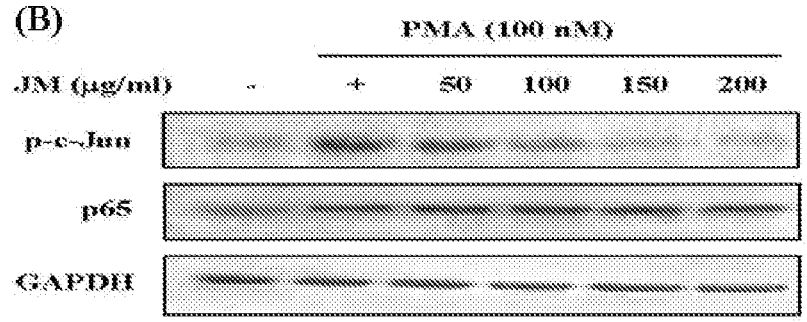

As shown in FIG. 6B, JM dramatically decreased AP-1 binding activity induced by PMA, but it did not affect the PMA-induced binding activity of NF-kB. These data suggest that JM inhibits PMA-induced MMP-9 expression by decreasing DNA binding activity of AP-1.

In subsequent experiment, the effect of JM on the PMA-induced phosphorylation of c-Jun, a major subunit of AP-1, and PMA-stimulated nuclear translocation of p65, a major subunit of NF-kB, which are required for the transcriptional activities was confirmed by Western blot analysis.

As the method described in example 3, Western blot analysis was performed using the specific antibodies against of p-c-Jun and p65 (Cell Signaling Technology, Danvers, Mass., USA).

As shown in FIG. 6B, PMA induced the nuclear translocation of p65 and phosphorylation of c-Jun and JM inhibited the phosphorylation of c-Jun in a dose-dependent manner. As expected, however, the nuclear translocation of p65 was not affected by JM.

Example 7

Effects of JM on PMA-Induced Activation of Mitogen-Activated Protein Kinase (MAPK) Signaling Pathways in MCF-7 Cells It is known that MMP-9 expression can be activated via a number of signal transduction pathways including those involving ERK1/2, p38 MAPK, and JNK, which are the upstream modulators of AP-1 or NF-kB (Cho, H J et al., Carcinogenesis, 28:1104, 2007, Woo, J H et al., Cancer Res. 63:3430, 2003).

To elucidate which of these signal transduction pathways are involved in PMA-stimulated MMP-9 expression and JM-mediated inhibition of the MMP-9 expression in MCF-7 cells, the effects of specific kinase inhibitors of these signaling pathways on the expression of MMP-9 in PMA-induced MCF-7 cells were examined using gelatin zymography.

Figure 7:
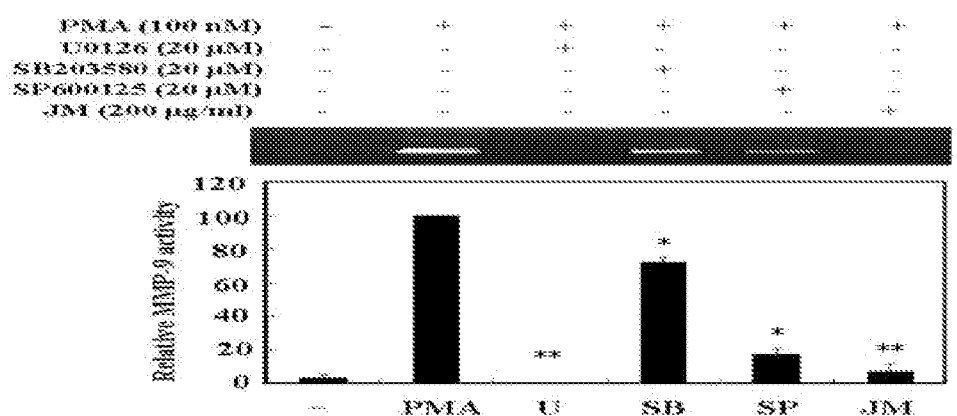
FIG. 7 shows Effects of JM on PMA-induced activation of mitogen-activated protein kinase (MAPK) signaling pathways.
Figure 7:
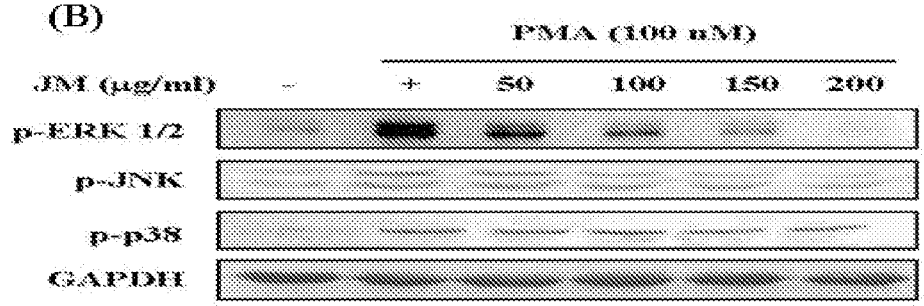

As shown in FIG. 7, PMA-induced MMP-9 expression was completely inhibited by treatment of selective inhibitor of ERK1/2 (U0126) and partly inhibited by selective inhibitors of p38 MAPK (SB203580) and JNK (SP600125).

PMA-induced MMP-9 expression was also inhibited by JM, similar to the effect of U0126.

To investigate which of ERK1/2, p38 MAPK and JNK pathways are involved in the inhibition of MMP-9 expression by JM, these pathways was confirmed by Western blot analysis using the specific antibodies against of ERK1/2, p38, MAPK and JNK (Cell Signaling Technology, Danvers, Mass., USA).

The treatment of JM specifically decreased ERK1/2 phosphorylation in a does-dependent manner, whereas the phosphorylation levels of JNK and p38 MAPK were slightly decreased by JM (FIG. 7B).

These data suggest that the specific inhibition of ERK1/2 signaling pathway are directly involved in the regulation of PMA-induced MMP-9 expression by JM.

INDUSTRIAL APPLICABILITY

As described above in detailed description, the anticancer composition containing an effective amount of herbal extract has advantage of minimal or few side effects and cytotoxicity when compared to many existing anticancer drugs having cytotoxicity and side effects.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. A method for treating breast cancer in a subject comprising the step of administering an effective amount of extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai*, to the subject, wherein the weight ratio of *Salviae Milfiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai* in the extract is 1:0.1-10:0.1-10:0.1-10:0.1-10:0.1-10:0.1-10:0.1-10:0.1-10:0.1-10:0.1-10:0.1-10, respectively, and wherein the concentration of the extract administered is less than or equal to 200 µg/ml.

2. A method for inhibiting MMP expression in a subject comprising the step of administering an effective amount of extract of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai*, to the subject, wherein the weight ratio of *Salviae Miltiorrhizae Radix, Chrysanthemum indicum, Acanthopanax senticosus, Cinnamomum cassia Blume, Eucommia ulmoides Oliv., Glycyrrhiza uralensis Fisch, Pueraria thunbergiana Benth, Crataegus pinnatifida Bunge, Cassia tora, Carthamus tinctorius* L., *Paeonia lactiflora Pall.* and *Angelica gigas Nakai* in the extract is 1:0.1-10:0.1-10:0.1-10:0.1-10:0.1-10:0.1-10:0.1-10:0.1-10:0.1-10:0.1-10:0.1-10, respectively, and wherein the concentration of the extract administered is less than or equal to 200 µg/ml.

3. The method of claim 1, wherein the extract comprises the root of *Salviae Miltiorrhizae Radix*, the flower of *Chrysanthemum indicum*, the seeds of *Acanthopanax senticosus*, the bark of *Cinnamomum cassia Blume*, the bark of *Eucommia ulmoides Oliv.*, the bark of *Glycyrrhiza uralensis Fisch*, the root of *Pueraria thunbergiana Benth*, the seeds of *Crataegus pinnatifida Bunge*, the seeds of *Cassia tora*, the flower of *Carthamus tinctorius* L., the root of *Paeonia lactiflora Pall.*, and the root of *Angelica gigas Nakai*.

4. The method of claim 2, wherein the extract comprises the root of *Salviae Miltiorrhizae Radix*, the flower of *Chrysanthemum indicum*, the seeds of *Acanthopanax senticosus*, the bark of *Cinnamomum cassia Blume*, the bark of *Eucommia ulmoides Oliv.*, the bark of *Glycyrrhiza uralensis Fisch*, the root of *Pueraria thunbergiana Benth*, the seeds of *Crataegus pinnatifida Bunge*, the seeds of *Cassia tora*, the flower of *Carthamus tinctorius* L., the root of *Paeonia lactiflora Pall.*, and the root of *Angelica gigas Nakai*.

5. The method of claim 1, wherein the extract is produced by extracting a powder with methanol to yield a methanolic extract, filtering the methanolic extract, concentrating the methanolic extract under reduced pressure, lyophilizing the methanolic extract, and dissolving the methanolic extract in dimethyl sulfoxide to yield the extract to be administered, wherein the powder comprises the root of *Salviae Miltiorrhizae Radix*, the flower of *Chrysanthemum indicum*, the seeds of *Acanthopanax senticosus*, the bark of *Cinnamomum cassia Blume*, the bark of *Eucommia ulmoides Oliv.*, the bark of *Glycyrrhiza uralensis Fisch*, the root of *Pueraria thunbergiana Benth*, the seeds of *Crataegus pinnatifida Bunge*, the seeds of *Cassia tora*, the flower of *Carthamus tinctorius L.*, the root of *Paeonia lactiflora Pall.*, and the root of *Angelica gigas Nakai*.

6. The method of claim 2, wherein the extract is produced by extracting a powder with methanol to yield a methanolic extract, filtering the methanolic extract, concentrating the methanolic extract under reduced pressure, lyophilizing the methanolic extract, and dissolving the methanolic extract in dimethyl sulfoxide to yield the extract to be administered, wherein the powder comprises the root of *Salviae Miltiorrhizae Radix*, the flower of *Chrysanthemum indicum*, the seeds of *Acanthopanax senticosus*, the bark of *Cinnamomum cassia Blume*, the bark of *Eucommia ulmoides Oliv.*, the bark of *Glycyrrhiza uralensis Fisch*, the root of *Pueraria thunbergiana Benth*, the seeds of *Crataegus pinnatifida Bunge*, the seeds of *Cassia tora*, the flower of *Carthamus tinctorius L.*, the root of *Paeonia lactiflora Pall.*, and the root of *Angelica gigas Nakai*.

\* \* \* \* \*

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
ggagccgctc tccaagaagc tt                                              22

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
ctcctccctt tcctccagaa cagaa                                           25

<210> SEQ ID NO 3
<211> LENGTH: 21
<212> TYPE: DNA
```

```
<213> ORGANISM: Artificial Sequence
<220> FEATURE:
<223> OTHER INFORMATION: Synthetic Construct

<400> SEQUENCE: 3
caagagatgg ccacggctgc t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
tccttctgca tcctgtcggc a                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tgacccctga gtcagcactt                                                20

<210> SEQ ID NO 6
<211> LENGTH: 17
<212> TYPE: DNA
<213> ORGANISM: Artificial Sequence
<220> FEATURE:
<223> OTHER INFORMATION: Synthetic Construct

<400> SEQUENCE: 6
ccagtggaat tccccag                                                   17
```